(12) United States Patent
Wang et al.

(10) Patent No.: US 9,907,660 B2
(45) Date of Patent: Mar. 6, 2018

(54) ORTHOPEDIC PAEK-ON-POLYMER BEARINGS

(75) Inventors: Aiguo Wang, Wayne, NJ (US); Zongtao Zhang, Riverdale, NJ (US); Daniel E. Lawrynowicz, Monroe, NY (US); Shi-Shen Yau, Berkeley Heights, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 868 days.

(21) Appl. No.: 12/793,184

(22) Filed: Jun. 3, 2010

(65) Prior Publication Data

US 2010/0312348 A1     Dec. 9, 2010

Related U.S. Application Data

(60) Provisional application No. 61/217,776, filed on Jun. 4, 2009.

(51) Int. Cl.
| | | |
|---|---|---|
| *A61F 2/32* | (2006.01) | |
| *A61F 2/38* | (2006.01) | |
| *A61F 2/30* | (2006.01) | |
| *A61L 27/16* | (2006.01) | |
| *A61L 27/18* | (2006.01) | |

(Continued)

(52) U.S. Cl.
CPC ............ *A61F 2/32* (2013.01); *A61F 2/30767* (2013.01); *A61F 2/38* (2013.01); *A61L 27/16* (2013.01); *A61L 27/18* (2013.01); *A61F 2/40* (2013.01); *A61F 2/42* (2013.01); *A61F 2/44* (2013.01); *A61F 2002/30014* (2013.01); *A61F 2002/30016* (2013.01); *A61F 2002/30067* (2013.01); *A61F 2002/30934* (2013.01); *A61F 2250/0018* (2013.01); *A61F 2250/0019* (2013.01)

(58) Field of Classification Search
USPC .......... 623/16.11, 18.11, 19.11–19.12, 20.21, 623/20.22, 20.29, 20.3, 20.31, 20.33, 623/21.13, 21.15, 21.16, 21.17, 21.18, 623/21.19, 22.11, 22.17, 22.18, 22.4, 623/23.39, 23.4, 23.41, 23.58, 23.59, 23.6
See application file for complete search history.

(56) References Cited

U.S. PATENT DOCUMENTS

| | | |
|---|---|---|
| 4,267,608 A | 5/1981 | Bora, Jr. |
| 5,092,896 A | 3/1992 | Meuli et al. |

(Continued)

FOREIGN PATENT DOCUMENTS

| | | |
|---|---|---|
| CN | 1114225 A | 1/1996 |
| CN | 101400383 A | 4/2009 |

(Continued)

OTHER PUBLICATIONS

European Search Report, EP 10164746, dated Oct. 5, 2010.

(Continued)

*Primary Examiner* — Marcia Watkins
(74) *Attorney, Agent, or Firm* — Lerner, David, Littenberg, Krumholz & Mentlink, LLP (57) ABSTRACT

An orthopedic prosthetic joint comprising a joint couple having a first bearing surface made of a poly aryl ether ketone (PAEK) and a second joint component having a second bearing made of a polymer that is softer than the PAEK such as UHMWPE the first and second bearing surfaces in sliding engagement with one another.

13 Claims, 12 Drawing Sheets

(51) Int. Cl.
*A61F 2/40* (2006.01)
*A61F 2/44* (2006.01)
*A61F 2/42* (2006.01)

(56) References Cited

U.S. PATENT DOCUMENTS

| | | | |
|---|---|---|---|
| 5,181,930 | A | 1/1993 | Dumbleton et al. |
| 5,326,354 | A | 7/1994 | Kwarteng |
| 5,370,696 | A | 12/1994 | Jamison et al. |
| 5,443,513 | A | 8/1995 | Moumene et al. |
| 5,645,605 | A | 7/1997 | Klawitier |
| 5,879,387 | A | 3/1999 | Jones et al. |
| 6,017,975 | A * | 1/2000 | Saum et al. ............... 522/161 |
| 6,087,553 | A | 7/2000 | Cohen et al. |
| 6,302,916 | B1 | 10/2001 | Townley et al. |
| 6,638,311 | B2 | 10/2003 | Wang et al. |
| 6,758,864 | B2 | 7/2004 | Storer et al. |
| 7,001,433 | B2 | 2/2006 | Songer et al. |
| 7,517,919 | B2 | 4/2009 | Wang et al. |
| 2002/0107300 | A1 | 8/2002 | Saum et al. |
| 2002/0111691 | A1 | 8/2002 | Wang et al. |
| 2003/0009222 | A1* | 1/2003 | Fruh et al. ............... 623/17.11 |
| 2003/0093152 | A1* | 5/2003 | Pedersen et al. ......... 623/14.12 |
| 2003/0208280 | A1* | 11/2003 | Tohidi ..................... 623/23.39 |
| 2004/0054411 | A1 | 3/2004 | Kelly et al. |
| 2004/0073310 | A1 | 4/2004 | Moumene et al. |
| 2004/0098127 | A1 | 5/2004 | Charlebois et al. |
| 2005/0021149 | A1 | 1/2005 | Borruto et al. |
| 2005/0033437 | A1 | 2/2005 | Bao et al. |
| 2005/0171610 | A1* | 8/2005 | Humphreys et al. ...... 623/17.15 |
| 2006/0167551 | A1 | 7/2006 | Stad |
| 2006/0178497 | A1 | 8/2006 | Gevaert et al. |
| 2006/0178749 | A1 | 8/2006 | Pendleton et al. |
| 2006/0212122 | A1 | 9/2006 | Perera |
| 2007/0027547 | A1 | 2/2007 | Rydell et al. |
| 2007/0073410 | A1 | 3/2007 | Raugel |
| 2007/0255412 | A1 | 4/2007 | Hajaj et al. |
| 2007/0100447 | A1 | 5/2007 | Steinberg |
| 2007/0142914 | A1 | 6/2007 | Jones et al. |
| 2007/0179615 | A1 | 8/2007 | Heinz et al. |
| 2007/0179618 | A1 | 8/2007 | Trieu et al. |
| 2007/0191962 | A1 | 8/2007 | Jones et al. |
| 2007/0270970 | A1 | 11/2007 | Trieu |
| 2007/0270971 | A1 | 11/2007 | Trieu et al. |
| 2008/0021557 | A1* | 1/2008 | Trieu ..................... 623/17.15 |
| 2008/0109081 | A1 | 5/2008 | Bao et al. |
| 2009/0164023 | A1 | 6/2009 | Devine |
| 2009/0326673 | A1 | 12/2009 | Devine et al. |
| 2010/0076114 | A1 | 3/2010 | Devine et al. |

FOREIGN PATENT DOCUMENTS

| | | |
|---|---|---|
| EP | 1647242 A1 | 4/2006 |
| EP | 1992309 A1 | 11/2008 |
| GB | 2319962 A | 6/1998 |
| WO | 2007/016795 A1 | 2/2007 |
| WO | 2007099307 A1 | 9/2007 |
| WO | 2008034135 A2 | 3/2008 |

OTHER PUBLICATIONS

Heather Austin, Wear of PEEK All-Polymer Articulations for Cervical Spinal Disc Arthroplasty, A thesis presented to the University of Waterloo in fulfillment of the thesis requirement for the degree of Master of Applied Science in Mechanical Engineering, 2008, Waterloo, Ontario, Canada.
Austin et al, Performance on PEEK All-Polymer Articulations for Spinal Applications, Paper No. 275, 56th Annual Meeting of the Orthopeadic Research Society, Mar. 6-9, 2010.
Bradley et al., Clinical Materials, 14, pp. 127-132, 1993.
International Search Report PCT/GB2007/000689, Jun. 5, 2007.
Jones et al., Proc. ImechE, vol. 223, Part H:J; Engineering in Medicine, 2009.
Kurtz et al., Biomaterials, 28, pp. 4845-4869, 2007.
Lee et al., Wear 267, 1915-1921, 2009.
Mathiesen et al., Acta Orthop Scand, 57, pp. 193-196, 1986.
McKellop et al., 31st Annual ORS, Las Vegas, Nevada, Jun. 21-24, 1985.
Morre et al., The Journal of Arthroplasty, vol. 13, No. 4, 1998.
Olagoke Olabisi, Handdook of Thermoplastics, Chapter 37, Cakmak, 931-950, Mar. 19, 1997.
Orthopedic Design & Technology, The PEEK of Large Joint Performance?, pp. 51-55, Mar./Apr. 2009.
Quadrant, Advanced Engineering Plastics for Life Sciences Applications, 2007.
Toru Moro, et al in Nature Materials, published online Oct. 24, 2004, p. 829-836.
Wang et al, Wear, (225-229), pp. 724-727, 1999.
Wang, Tribology International, vol. 31, No. 11, pp. 661-667, 1998.
Coats, Larry, two letters dated May 29, 2012 from the law firm of Coates+Bennett PLLC of 1400 Crescent Green, Suite 300 Cary, North Carolina 27518.
Third Party Obeservations for for European Patent Application No. 10164746.9 dated Jun. 12, 2012.
Third Party Obeservations for for European Patent Application No. 10164746.9 dated Aug. 31, 2012.
Coats, Larry L., Letter from Coats + Bennett PLLC dated Jan. 29, 2013.
Canadian Office Action for Application No. 2,706,233 dated Nov. 14, 2012.
Chinese Office Action for Application No. 201010192020.5 dated Dec. 11, 2013.
Third Party Observations for European Patent Application No. 10164746.9 dated Mar. 3, 2014.
Opposition against Australian Application No. 2010202320 dated Mar. 1, 2017, 2 pages.
Statement of Grounds and Particulars for Australian Application No. 2010202320 dated Feb. 28, 2017.
Extended European Search Report for Application No. 15191252.4 dated Mar. 22, 2016.
Decision in Australian Patent Opposition for Application No. 2010202320 dated Apr. 7, 2016.
"X3 Advanced Bearing Technology Monograph / Material Characteristics and Properties", Stryker Orthopaedics, Jan. 2007, Copyright 2007, 12 pages.
Brach del Prever et al., "UHMWPE for arthroplasty: past or future?", J. Orthopaed Traumatol (200(0 10:1-8.
Opposition against European Patent No. 2258319 (Application No. 10164746.9) in the name of Howmedica Osteonics Corp. dated Oct. 5, 2016, 39 pages.
Stein L. Harvey, "Ultra High Molecular Weight Polyethylene (UHMWPE)", Engineering Materials Handbook, vol. 2: Guide to Engineering Plasctics Families: Thermoplastic Resins, ASMInternational, Copyright 1992, Revised 1999, pp. 167-171.
Waybackmachine extract of Stryker website, Stryker Orthopaedics, Nov. 24, 2008, 5 pages.

* cited by examiner

ORTHOPEDIC PAEK-ON-POLYMER BEARINGS

CROSS-REFERENCE TO RELATED APPLICATIONS

This application claims the benefit of the filing date of U.S. Provisional Patent Application No. 61/217,776 filed Jun. 4, 2009, the disclosure of which is hereby incorporated herein by reference.

BACKGROUND OF THE INVENTION

Polyaryl ether ketones (PAEK), such as PEEK, which is the most commercialized, are well known polymers such as described in Chapter 37 of the "Handbook of Thermoplastics" published by Marcel Dekker Inc. These polymers are highly aromatic mostly semi crystalline thermoplastics which, because of their aromatic polymer backbone, have transition temperatures as high as 240° C. These polymers may be synthesized by well known condensation polymerization methods. PAEK has excellent resistance to acids, water and is capable of being sterilized by gamma radiation, ethylene oxide gas and steam.

Reinforced polyetheretherketone (PEEK) has been proposed for us in orthopedic implants such as hip stems and acetabular cups. U.S. Pat. Nos. 5,181,930 and 5,443,513 relate to hip stems made of PEEK including carbon fiber reinforcements. PEEK has also been proposed for use in acetabular cups as either backing or bearing materials. See for example, U.S. Pat. Nos. 6,638,311 and 6,758,864. Flexible acetabular cups made of PEEK have also been proposed as discussed in U.S. Publications 2007/073410 and 2007/0191962. In these proposals the opposite bearing, such as a femoral head, have been made of either a ceramic or metal bearing surface.

U.S. Patent Publication 2009/0164023 relates to an all polymeric bearing couple wherein each part is made of a composite material including carbon fiber reinforcement.

PEEK and carbon fiber reinforced PEEK composite as a potential bearing surface for total joint replacement applications was considered in the 1990s (Wang, A., Lin, R., Stark, C., and Dumbleton J H., Wear 225-229 (1999) 724-727). The intention was to replace the ultrahigh molecular weight polyethylene bearing (UHMWPE) with PEEK or carbon fiber reinforced PEEK composite bearings in traditional metal or ceramic-on-UHMWPE bearing couples for total hip and total knee joint replacements. It was found that pure PEEK without carbon fiber reinforcement against a ceramic counterface produced higher wear rate than a traditional ceramic-on-UHMWPE bearing couple while a ceramic-on-carbon fiber reinforced PEEK composite yielded a lower wear rate than a traditional ceramic-on-UHMWPE bearing couple. Metallic bearing counterfaces such as CoCr or stainless steel was found unsuitable against carbon fiber reinforced PEEK composite bearing due to significant scratching of the metallic surface by the harder carbon fibers. Carbon fiber reinforced PEEK-on-PEEK has only been considered for either smaller non-weight bearing or low weight-bearing joints (Qi-Bin Bao, et al, Nubac Disc Arthroplasty: Preclinical studies and preliminary safety and efficacy evaluations, SAS Journal, Winter 2007, Volume 01, issue 01, p. 36-45). A low-to-high wear transition was found for PEEK-on-PEEK as the applied load increased in a wear test study (Heather Austin, et al, Exploring the wear of a peek all-polymer articulation for spinal application, Society for Biomaterials 2009 annual meeting, Apr. 22-25, 2009, San Antonio, Tex.).

PTFE-on-PTFE was first used for total hip replacement by Dr. John Charnley prior to 1962 (Steven M. Kurtz, The UHMWPE Handbook, p. 53-70). Because of poor wear performance; PTFE-on-PTFE has been abandoned. US patent publications 2007/0270970 and 971 relate to polymeric spine bearing components.

Polyacetal-on-Polyethylene was introduced as an all polymer bearing couple in total knee arthroplasty in the 1980's and clinical results were published in the 1990's (1) H. McKellop, et al, Super wear properties of an all-polymer hip prosthesis, 31$^{st}$ Annual ORS, Las Vegas, Nev., Jun. 21-24, 1985, page 322; (2) D. J. Moore, et al. The total knee replacement prosthesis may be made entirely of polymer. The Journal of Arthroplasty, Vol. 13, No. 4, 1998). Because poor gamma sterilization resistance of the polyacetal material (Delrin) and inadequate fixation of the Delrin femoral component to the bone, the use of Polyacetal-on-Polyethylene has been discontinued.

BRIEF SUMMARY OF THE INVENTION

This invention relates to PAEK-on-polymer (such as ultra high molecular weight polyethylene (UHMWPE) bearing couples, particularly PEEK (polyetheretherketone) on ultra high molecular weight polyethylene (UHMWPE). PAEKs (polyaryletherketones), include PEK (polyetherketone, PEKK (polyetherketoneketone), and PEKEKK (polyarylether-ketone-ether-ketone-ketone) and PEEK. If a PEEK bearing is used it can be a stand-alone pure PEEK component, a PEEK layer coated, molded or grafted onto another solid or porous polymer or polymeric composite substrate, or a PEEK layer coated, molded, or grafted onto a solid or porous metallic or ceramic substrate. The polymer bearing can be any kind of polymer that is softer than the PAEK. The polymer includes but not limited to polyethylene, polyurethane, polyamide, the composite of the polymers, etc. The polymer may be mono-polymer, co-polymer, surface grafted polymer or coated polymer. More specifically, this invention relates to non-carbon fiber reinforced PEEK-ON-UHMWPE as a bearing couple for orthopaedic applications. The bearings are used in artificial joints that replace biological joints such as hips, knees, shoulders, elbows, fingers and spine.

This invention uses pure (un-reinforced especially non-carbon fiber reinforced) PEEK, or a PAEK polymer with similar properties, to replace the typical metal or ceramic as one of the bearing surfaces in a metal-on-polymer or ceramic-on-polymer pair. It has unexpectedly been found that PEEK-on-polymer bearing couples (such as PEEK-on-polyethylene) have lower wear rates than typical orthopedic bearing couples (such as metal-on-polyethylene). The mechanism of the low wear rate of PEEK-on-polymer may be contributed to two mechanisms. (1) Less total contact stress. Since the PEEK has a much lower Young's modulus than CoCr, the PEEK has high elastic deformation under the same compressive force, which may facilitate elastohydrodynamic lubrication than conventional metal or ceramic on polymer joints. (2) Local sharpness effect: The wear takes place when two surfaces contact and rub each other. The wear rate is highly determined by the sharpness and hardness of the surface asperities under standard body contact force and wet lubrication. PEEK has very low hardness (about Shore D 85) as compared to CoCr alloy (Vickers 450), thus the asperities of PEEK are blunt and compressible, while the CoCr— is sharp and stiff. The blunt asperities wear the counter surface less than the sharp ones.

The present invention provides a low cost bearing to replace traditional metal or ceramic bearings in use for many years. Injection-molded, compression molded or extruded PEEK material is a low cost bearing because of cost-effective manufacturing. However, there was concern among those skilled in the art about potentially poor scratching resistance of the PEEK as compared to metal or ceramic as well as potential stiction between two polymer surfaces. Coating a ceramic or metallic layer on PEEK femoral heads and on PEEK knee femoral components was attempted and Metal and ceramic heads coated with PEEK have been previously produced and tested by the inventors herein. However the overall bonding of the hard metal and ceramic coating to the soft PEEK substrate has not been good. As a result, the hard coating approach was abandoned. Instead, grafting a lubrication film (MPC as described by Toro Moro, et al., Nature Materials, published online 24 Oct. 2004, pp. 829-836) on UHMWPE was attempted to decrease friction and wear. MPC was grafted according to the process parameters from known literature on X3™ UHMWPE is a trademark of Stryker Corp. of sequentially cross-linked polyethylene as described in U.S. Pat. No. 7,517,919 the disclosure of which is incorporated herein by reference. The UHMWPE used herein has been crosslinked three times as described in the '919 Patent. $N_2VAC$, as used herein, is UHMWPE which has been crosslinked by a single 3 MRad dose of radiation in nitrogen with less than 1% oxygen. Wear tests were conducted in a hip joint wear simulator with pure PEEK femoral heads articulating against the MPC grafted polyethylene cups.

The initial purpose of the wear tests was to determine whether PEEK-on-UHMWPE with MPC grafting was workable, while the PEEK-on-non-grafted UHMWPE and CoCr-on-non-grafted UHMWPE were used as controls. It was hypothesized that the MPC grafting on UHMWPE would be necessary to enable the PEEK-on-UHMWPE bearing couple to match the wear performance of the traditional CoCr-on-UHMWPE couple. However, the PEEK-on-UHMWPE with the MPC grafting removed had better wear performance than CoCr-on-UHMWPE. This was unexpected. Further experiments were conducted using completely PEEK heads replacing the Colbat chrome heads against $N_2VAC$ and showed a significantly decreased wear rate. These results demonstrated that PEEK heads as the harder bearing couple has superior results over CoCr heads against UHMWPE regardless of the degree of crosslinking on the UHMWPE.

One aspect of this invention is to provide a better artificial bearing couple that has the advantages of low wear, low-stiffness, no metal ions release, and lower manufacturing cost, over traditional metal-on-polymer, metal on metal and ceramic-on-polymer bearings.

There had been no PEEK-on-polyethylene bearing couples prior to the present invention for orthopedic applications. Other types of well known bearings are: (1) Metal or ceramic-on-carbon fiber reinforced PEEK, (2) PEEK-on-PEEK (PEEK against itself for finger and spine joints), (3) Polyacetal-on-polyethylene, and (4) PTFE-on-PTFE (Steven M. Kurtz, UHMWPE handbook, Elsevier Academic press, New, York, 2004).

The lower wear rate found herein for PEEK-on-UHMWPE (compared to metal-on-UHMWPE) opened up the possibility for the first time to replace the metal counterpart in the traditional metal-on-UHMWPE bearing couple. Prior to our discovery of the unexpected superior wear performance of PEEK-on-UHMWPE, there had been no reported studies considering that bearing couple for orthopaedic applications. Most previous studies on PEEK as a bearing surface including those of the inventor of the present invention focused on using PEEK to replace UHMWPE as the sacrificial bearing against metal or ceramic counterface while no one had considered replacing the metal or ceramic counterface with PEEK against UHMWPE. The novelty of the present invention is that PEEK is the non-sacrificial counterface while UHMWPE is the sacrificial one.

In addition to the lower wear rate for the PEEK-on-UHMWPE bearing couple as compared to the traditional metal-on-UHMWPE couple, PEEK has an elastic modulus between those of subcondra bone and cortical bone, which enables more physiologic load transfer to implant and bone interfaces and potentially reduces or even eliminates stress-shielding as seen in conventional metal or ceramic implants.

Since the PEEK-on-UHMWPE bearing couple is all polymeric, it does not involve metal as a bearing surface and there is, therefore, no metal ions release at all and no concern for potential metal hyper-sensitivity as seen in some patients with a metal-on-polymer or metal-on-metal implant.

PEEK has much higher oxidation and hydrolysis resistances than polyacetal in joint fluid, there is no oxidation or hydrolysis issue for PEEK-on-polyethylene bearing couples.

Compared to the PEEK-on-PEEK bearing couple, which has been considered for low weight bearing smaller joints such as the finger joints and the spine, the PEEK-on-UHMWPE bearing couple of the present invention can be used for both small and large weight bearing joints with both conforming bearing designs such as ball-in-socket joints (hips, spines and shoulders) and non-conforming bearing designs (knees, elbows, etc).

The present invention also relates to using PEEK as the softer part of a bearing couple and instead using PEEK as the harder part of the bearing articulating against a softer UHMWPE surface. This potentially eliminates many clinical problems such as those related to bearing surface wear, metal hypersensitivity, toxicity of metal ion release and bone stress-shielding associated with much stiffer metal or ceramic implants. Note that while sequentially crosslinked UHMWPE per U.S. Pat. No. 7,517,919 was used in combination with PEEK as a bearing couple herein as an example, any UHMWPE whether crosslinked or not, could be utilized.

DETAILED DESCRIPTION

Figure 1:
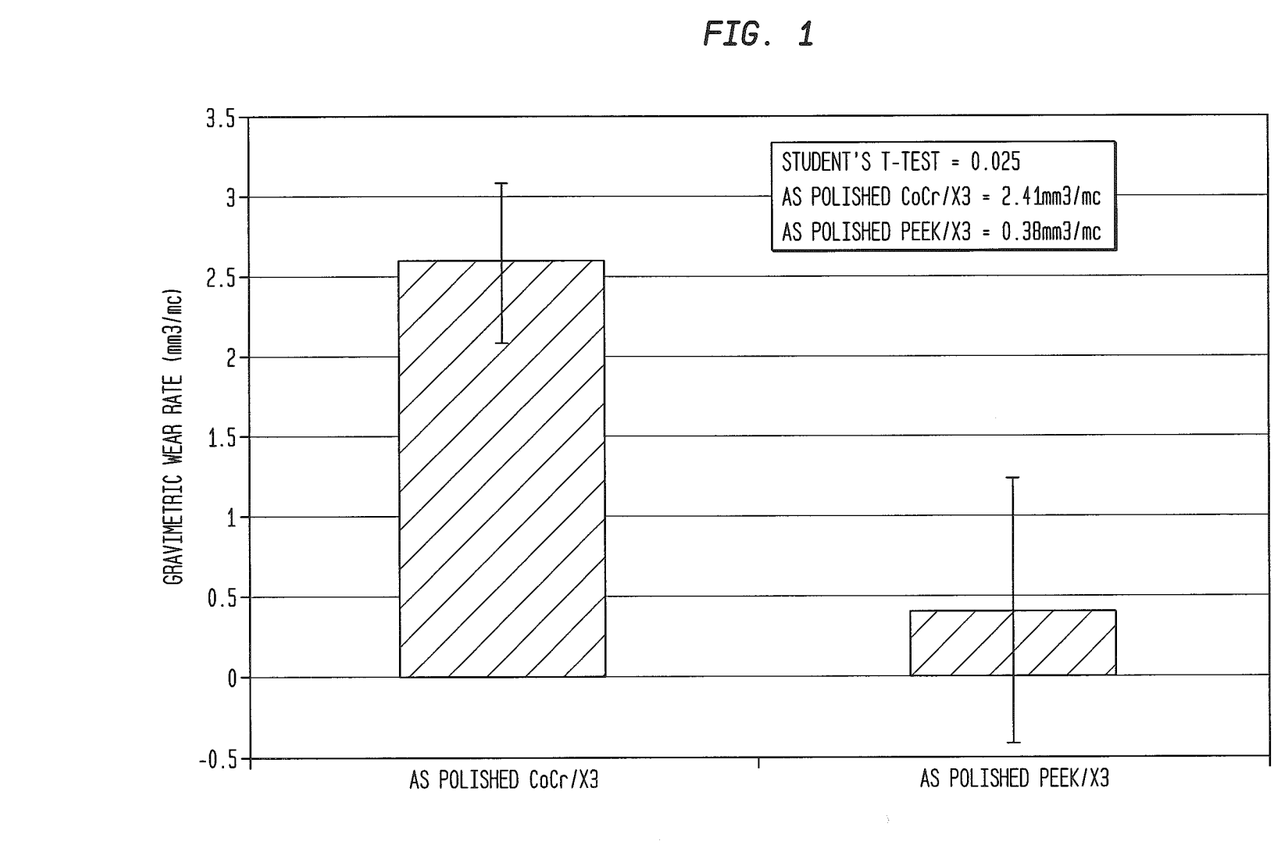
FIG. 1 is a graph showing the wear of a Cobalt Chrome alloy and a non-reinforced PEEK 32 mm femoral head on a cup of X3™ UHMWPE which have been crosslinked three times for 1.25 million cycles.

FIG. 1 shows a hip simulator wear results with as-polished femoral heads. This figure shows that X3™ UHMWPE cup in a CoCr-on-UHMWPE couple has a positive volumetric wear rate about 2.41 mm$^3$/million cycles (Mc), while the X3™ UHMWPE cup in the PEEK-on-X3™ UHMWPE couple with a polished PEEK head is only 0.38 mm$^3$/million cycles (Mc). The average wear rate of X3™ UHMWPE cup in the PEEK-on-X3™ against the as-polished PEEK femoral head is about 84% less than that against the as-polished CoCr femoral head. This difference in wear rate is statistically significant (Student's t-test, P=0.025). The wear rate of the PEEK head was not measurable using the gravimetric technique.

Figure 2:
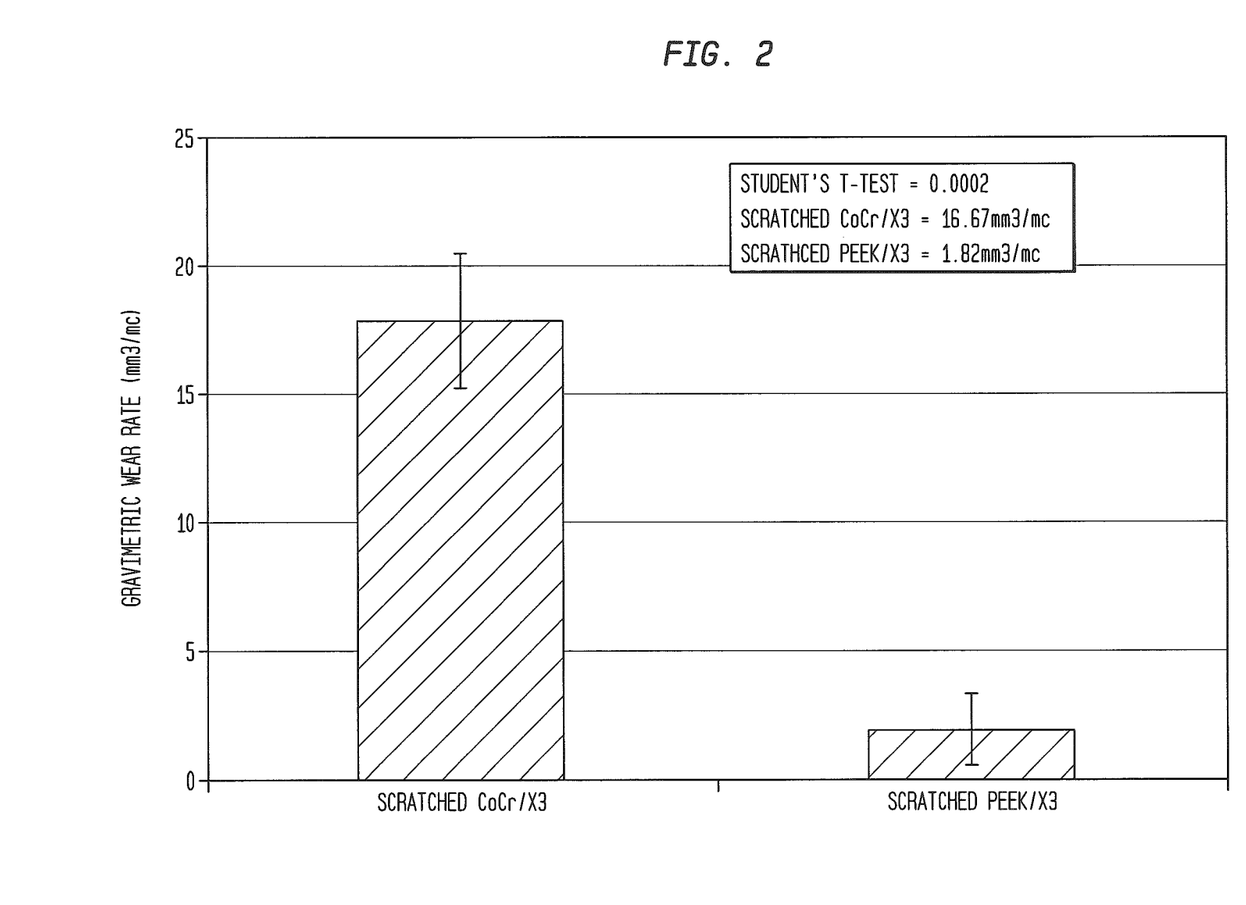
FIG. 2 is a graph showing test results similar to those in FIG. 1 but the femoral heads having been scratched.

FIG. 2 shows hip simulator wear results with intentionally scratched femoral heads. The average wear rate of the highly crosslinked polyethylene cup against the scratched PEEK head is about 1.82 mm$^3$/million cycles (Mc) while the average wear rate of X3™ UHMWPE cup against the scratched CoCr head is about 16.67 mm$^3$/million cycles (Mc). This represents an 89% lower wear rate for the highly crosslinked polyethylene cup against the scratched PEEK head than that against the scratched CoCr head. This difference in the wear rate is statistically significant (Student's t-test, P=0.0002). In fact, the average wear rate of the highly crosslinked polyethylene cup against the scratched PEEK head is statistically insignificantly different from that against as-polished PEEK head (Student's t-test, P=0.20), which indicates that the PEEK-on-highly crosslinked polyethylene bearing couple is insensitive or immune to scratching of the PEEK head. In contrast, scratching of the CoCr head caused an almost 7 fold increase in the wear rate of the highly crosslinked polyethylene cup (Student's t-test, P=0.0009).

Figure 3:
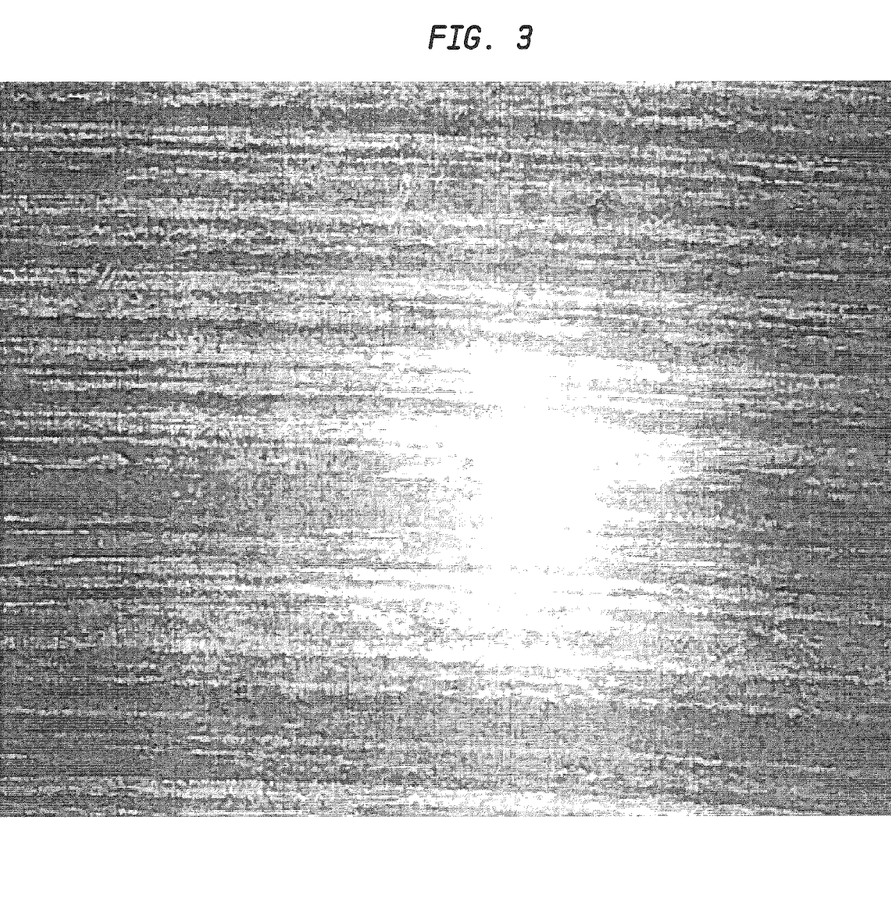
FIG. 3 is a photograph of the UHMWPE cup of FIG. 1 prior to wear testing.

FIG. 3 shows white light microscopy of a typical X3™ UHMWPE cup prior to wear testing (unworn cup). Before the hip simulator wear test, machining marks are clearly seen. Surface peak height is about 5160 nm, valley depth about −4758 nm and average roughness about 998 nm (Ra).

Figure 4:
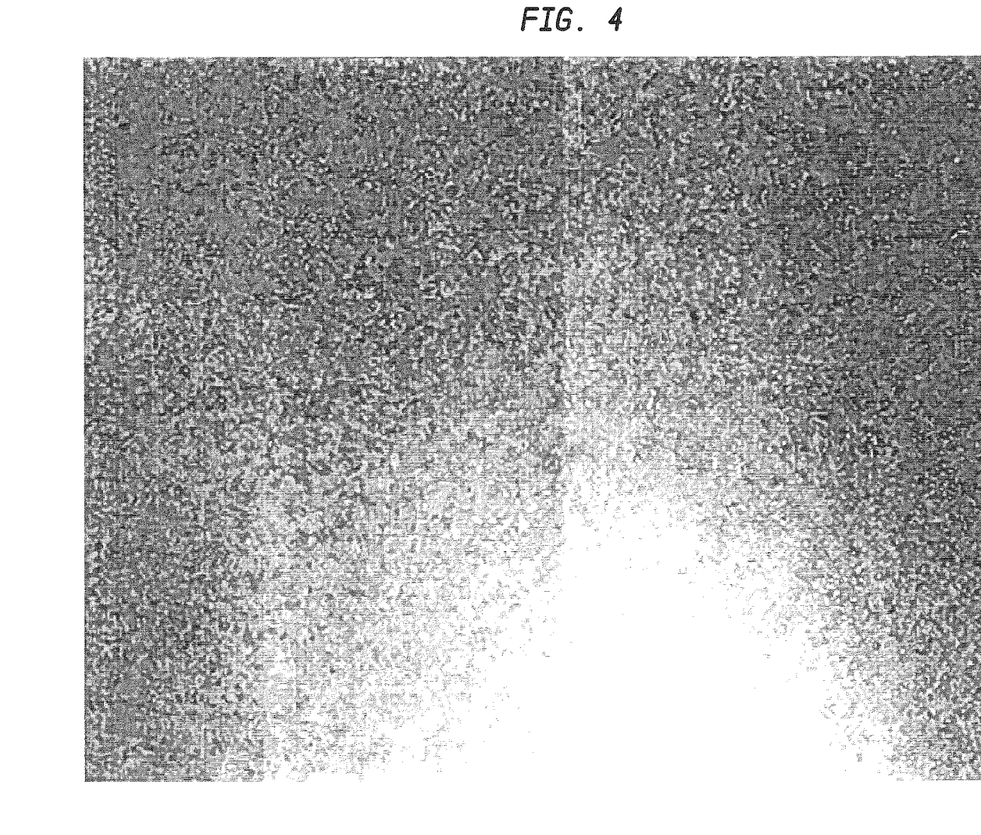
FIG. 4 is a photograph of the UHMWPE cup used against the CoCr head of FIG. 1 after wear testing.

FIG. 4 shows white light microscopy of the worn surface of a X3™ UHMWPE cup in the CoCr-on-UHMWPE couple with a polished CoCr head after 1.25 million cycles hip simulator wear testing. The machining marks are gone. Surface peak is 950 nm high, valley 1207 nm deep, and average roughness Ra=80 nm.

Figure 5:
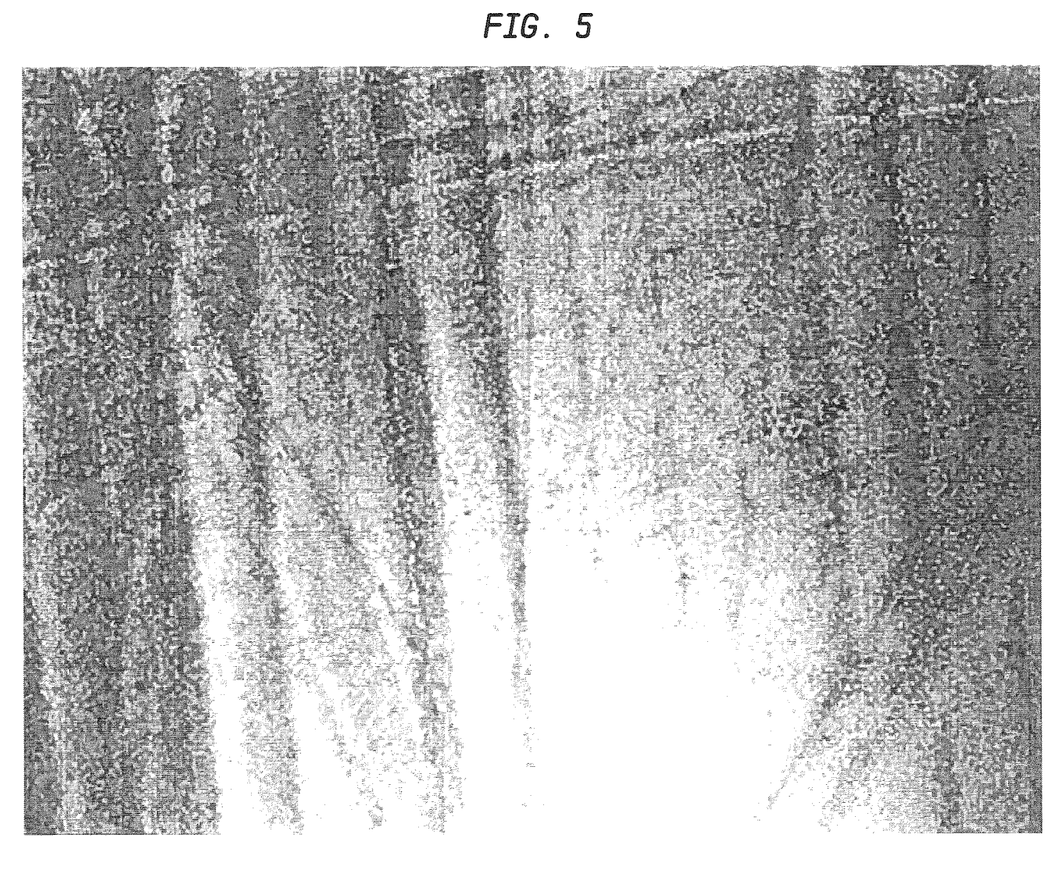
FIG. 5 is a photograph of UHMWPE cup used against the un-reinforced PEEK head of FIG. 1.

FIG. 5 is a white light microscopy of the worn surface of a X3™ UHMWPE cup in the PEEK-on-UHMWPE couple with a polished PEEK head after 1.25 million cycles hip simulator wear testing. Machining marks are still visible. Surface peak is 1872 nm high, valley 2715 nm deep, and an average roughness Ra=335 nm.

Figure 6:
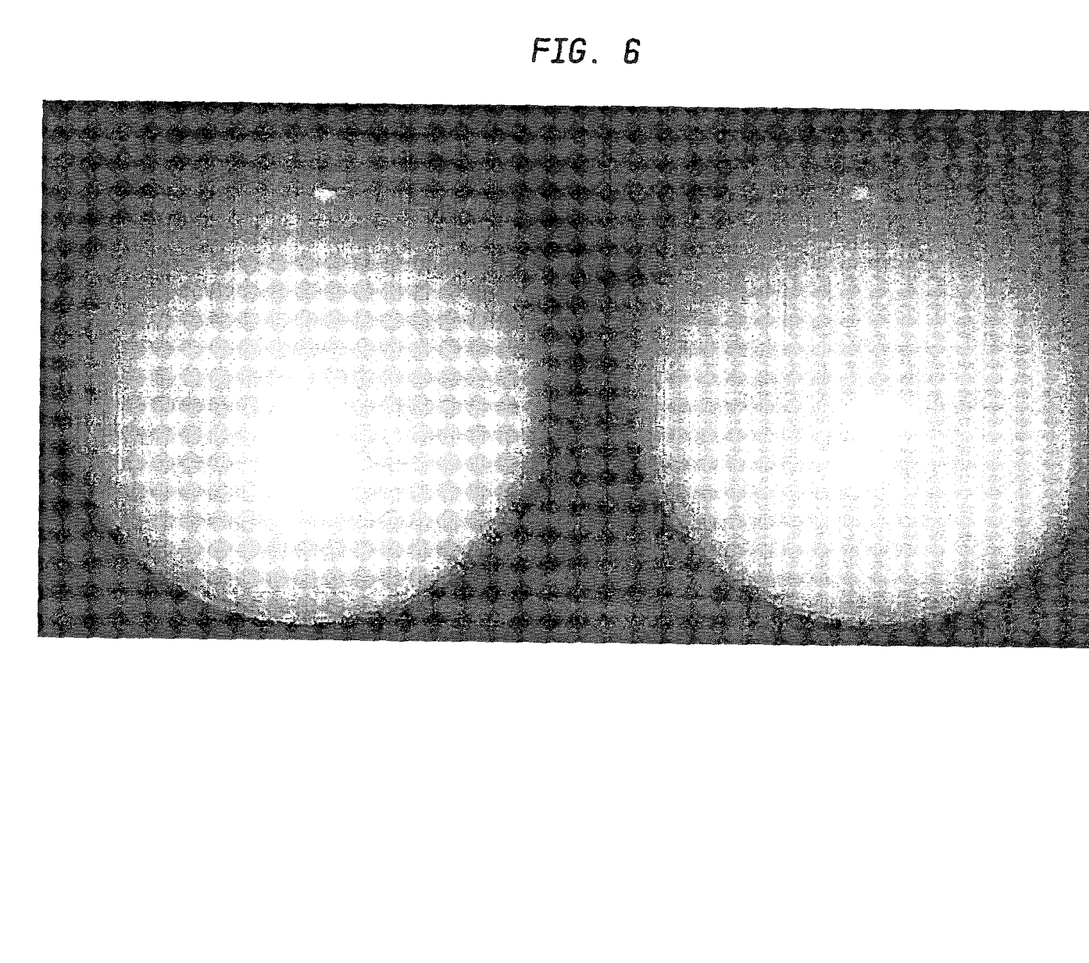
FIG. 6 shows photographs of unscratched PEEK head before and after testing.

FIG. 6 shows a photograph of an as-polished PEEK head before and after wear testing. No wear scar or roughening was found.

Figure 7:
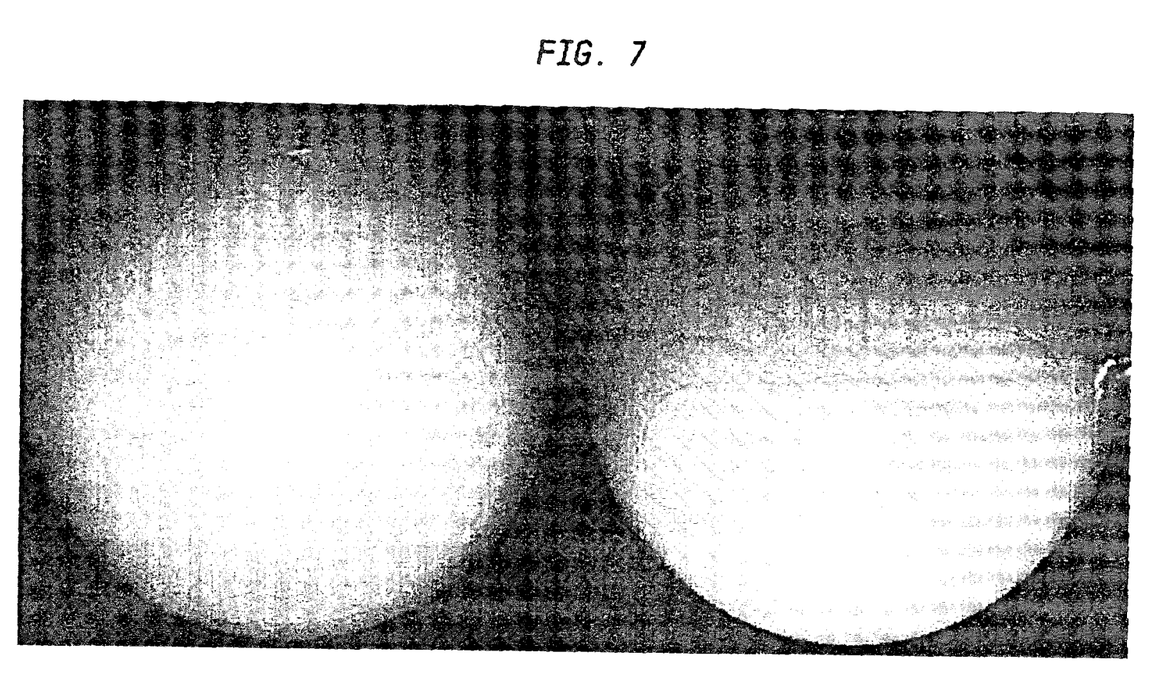
FIG. 7 shows photographs of a scratched PEEK head before and after testing.

FIG. 7 shows a photograph of the intentionally scratched PEEK head before and after wear testing. All scratching marks are still clearly visible on the head after 1.25 million cycles of testing.

EXAMPLE 1

A 1.5" diameter pure PEEK extruded rod was purchased from McMaster with the brand name "Quadrant Ketron®1000 (Reading, Pa.)", and machined into 32 mm diameter femoral heads. The 32 mm PEEK heads were polished to an average surface roughness of Ra=20 nm. Three 32 mm PEEK heads were tested against three 32 mm sequentially crosslinked UHMWPE cups in a hip simulator under maximum load of 2450 N at 1.0 HZ in 50% diluted Alpha Calf serum lubricant. Three 32 mm CoCr heads against three 32 mm X3™ UHMWPE cups were conducted in the same wear test as a control.

Wear results of the sequentially crosslinked polyethylene cup (X3) (about shore D 70) against as-polished CoCr (Vicher 450) and PEEK heads (about shore D 85) at 1.75 million cycles on the hip simulator are shown in FIG. 1. The X3™ UHMWPE cup in a PEEK-on-UHMWPE wear couple had an average wear rate of about 0.38 mm$^3$/million cycles (Mc), while the cup in CoCr-on-UHMWPE wear couple had an average wear rate of about 2.41 mm$^3$/million cycles (Mc), which represents an 84% lower wear rate for the PEEK-on-UHMWPE couple. This difference is statistically significant (Student's t-test, P=0.025).

EXAMPLE 2

Everything was the same as in Example 1, except 32 mm PEEK heads were intentionally scratched and then wear tested against 32 mm X3™ UHMWPE cups. White light microscopy showed that peak-to-valley height of the scratches was about 25 micron (μm), which is much higher than the 3.5 micron for a CoCr head scratched in the same way. The wear results indicated that the scratched 32 mm PEEK heads articulating against 32 mm sX3™ UHMWPE cups had an average wear rate of 1.82 mm$^3$/Mc (FIG. 2). By comparison, the non-scratched CoCr-on-X3™ UHMWPE pair showed a higher wear rate (2.41 mm$^3$/Mc, see FIG. 1). A more direct comparison was to use scratched CoCr heads against X3™ UHMWPE cups, which had an average wear rate of about 16.67 mm$^3$/Mc, according to R. Lee, A. Essner, A. Wang, W. L Jaffe available online 2 Apr. 2009 "Scratch and Wear Performance Of Prosthetic Femoral Head Components Against Crosslinked UHMWPE Sockets" (Wear, 2009). This means that scratching the PEEK bearing surface does not significantly affect the wear of X3™ UHMWPE part. This may be due to:
1. lower contact stress
2. self-polishing between PEEK and polyethylene, reducing harmful effect of scratching as often seen with metal surfaces
3. less rigid and less sharp scratches on the PEEK head

EXAMPLE 3

Everything was the same as Example 1, except 40 mm PEEK heads were rotated against 44 mm X3™ UHMWPE cups, which is a size mismatch done to simulate a non-conforming joint such as a knee joint. This mismatched PEEK-on-X3™ UHMWPE pair did not have a measurable wear rate (gravimetric weight gain more than weight loss). In comparison, the wear rate of the perfectly matched 32 mm X3™ UHMWPE cup against 32 mm CoCr head was measurable (2.41 mm³/Mc as shown in FIG. 1).

EXAMPLE 4

Everything was the same as in Example 1, except 32 mm PEEK heads were rotated against 32 mm X3™ UHMWPE cups that were grafted by MPC (2-methacryloyloxyethyl phosphsrylcholine, a biocompatible phospholipid, as described by Toru Moro, et al in Nature Materials, published online: 24 Oct. 2004, p. 829-836). This pair showed no measurable wear.

EXAMPLE 5

Figure 8:
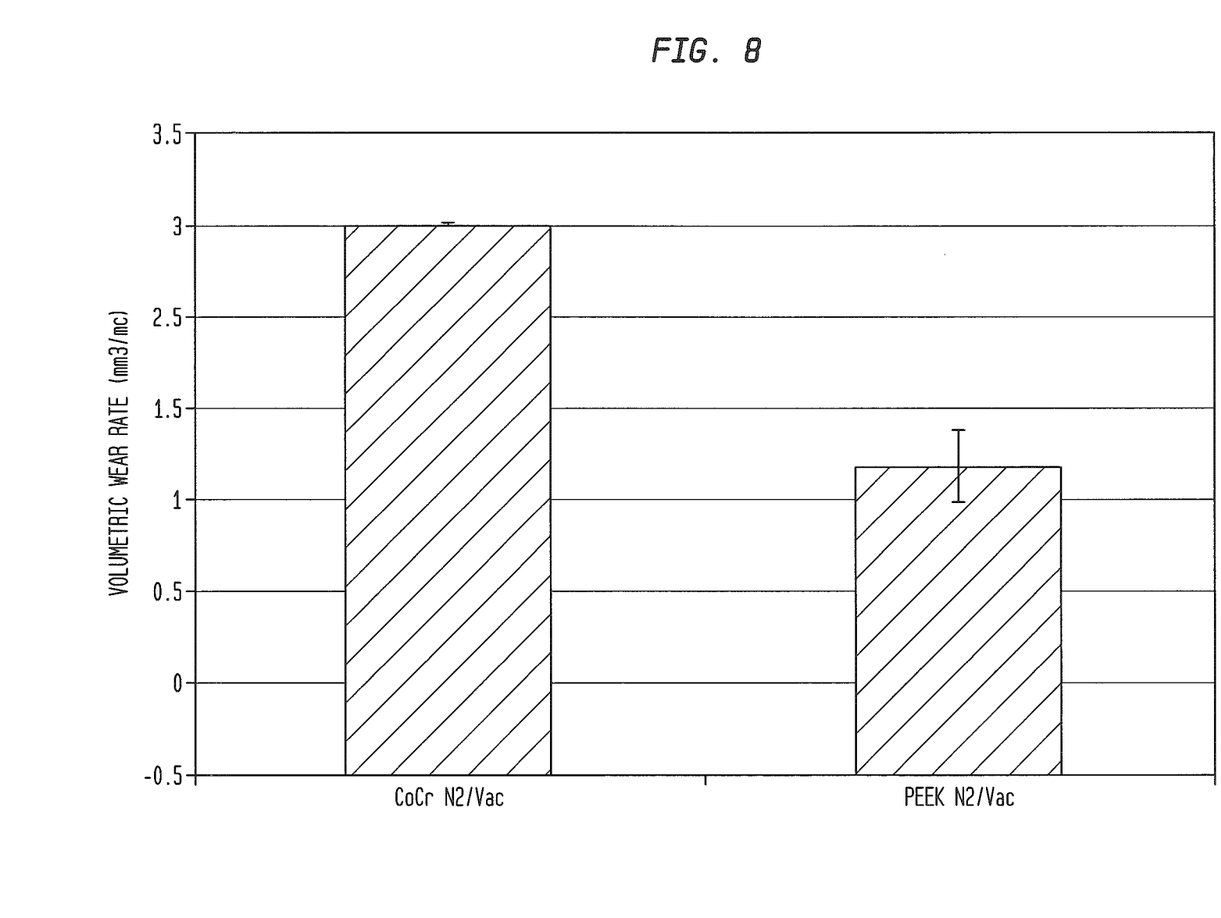
FIG. 8 is a comparison of CoCr and PEEK heads against $N_2Vac$ cross-linked UHMWPE.

PEEK-N2\Vac: 4.0 million cycle wear study on 28 mm PEEK components on UHMWPE irradiated at 3 MRad in nitrogen with less than 1% oxygen ($N_2$\Vac), N2\Vac D size cups found a wear rate of 16.6 mm³/mc was measured (SD 1.8; n=7). For comparison, study (HIP231) tested 28 mm CoCr heads on N2\Vac cups for a wear rate of 30.0 mm³/mc at 3.0 million cycles (SD 0.022; n=2) This corresponds to a statistically significant reduction in wear of 45% as shown in FIG. 8 ($p<0.05$).

EXAMPLE 6

PEEK-X3

Figure 9:
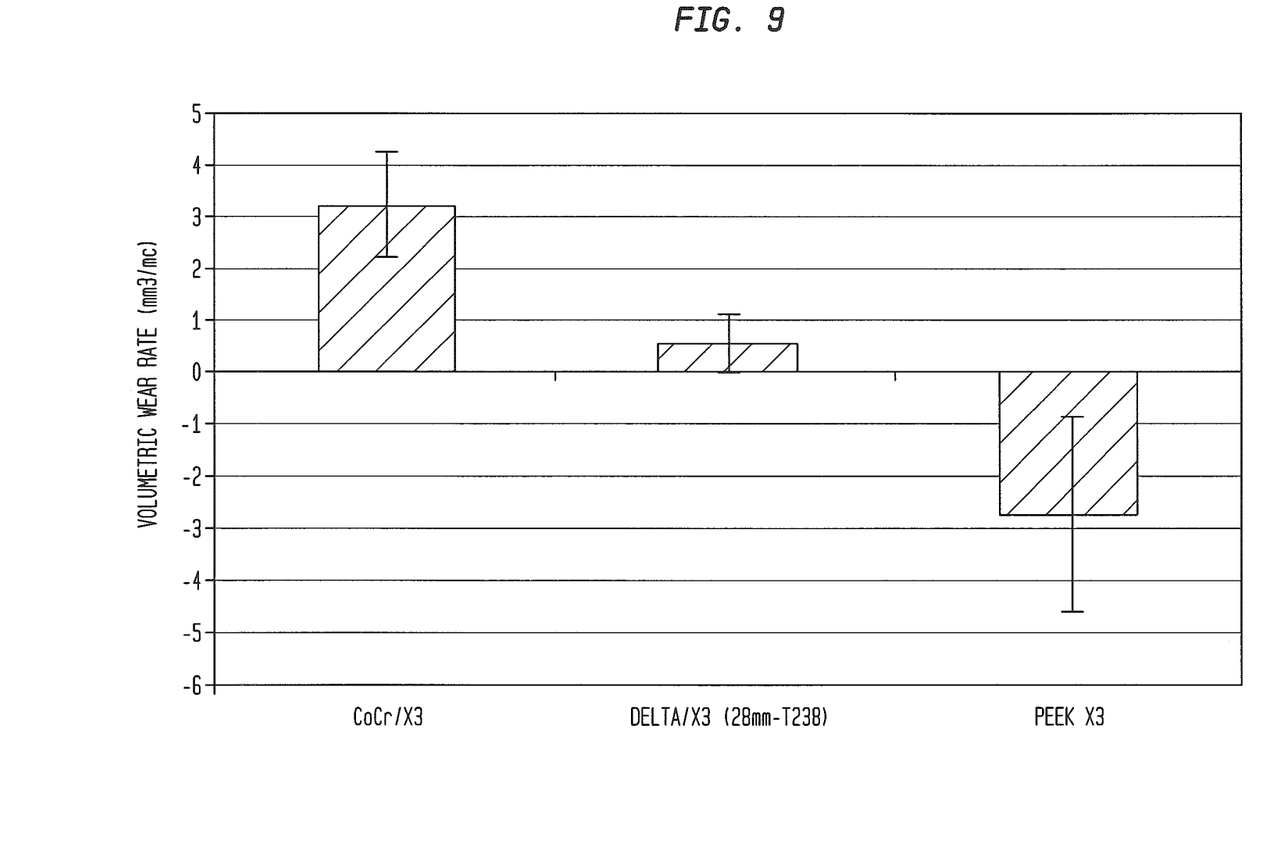
FIG. 9 is a comparison of a ceramic Alumina, 25% ZnO$_2$ Delta head against X3™ UHMWPE for a 28 mm head.

5.0 million cycle wear study (HIP284) on 32 mm PEEK components on X3™ UHMWPE D size cups, a wear rate of −2.75 mm³/mc was measured (SD 1.86; n=3) as shown in FIG. 9. The wear rate of CoCr, Delta and PEEK/x3, Delta/X3 were taken from a previous study for 28 mm heads. Despite dynamically loaded and temperature compensated soaking controls, the X3™ UHMWPE cup tested against a PEEK head did not show weight loss. For comparison, previously published wear rates for Delta ceramic on X3™ UHMWPE cup (28 mm; n=3) are also shown in the chart (0.55 mm³/mc SD 0.58). Machining marks were also still visible at 3.5 million cycles on the X3™ UHMWPE cups when tested against the PEEK head (FIG. 10) while machining marks were invisible at 0.75 mc when tested against CoCr heads (FIG. 11).

Figure 10:
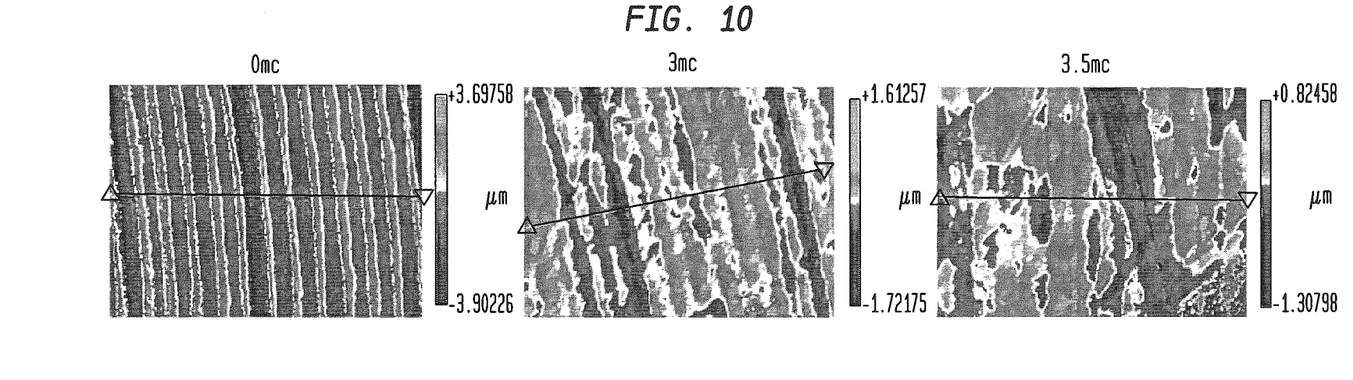
FIGS. 10 and 11 are photographs of the UHMWPE bearing before and after wear testing with PEEK and CoCr heads respectively.
Figure 11:
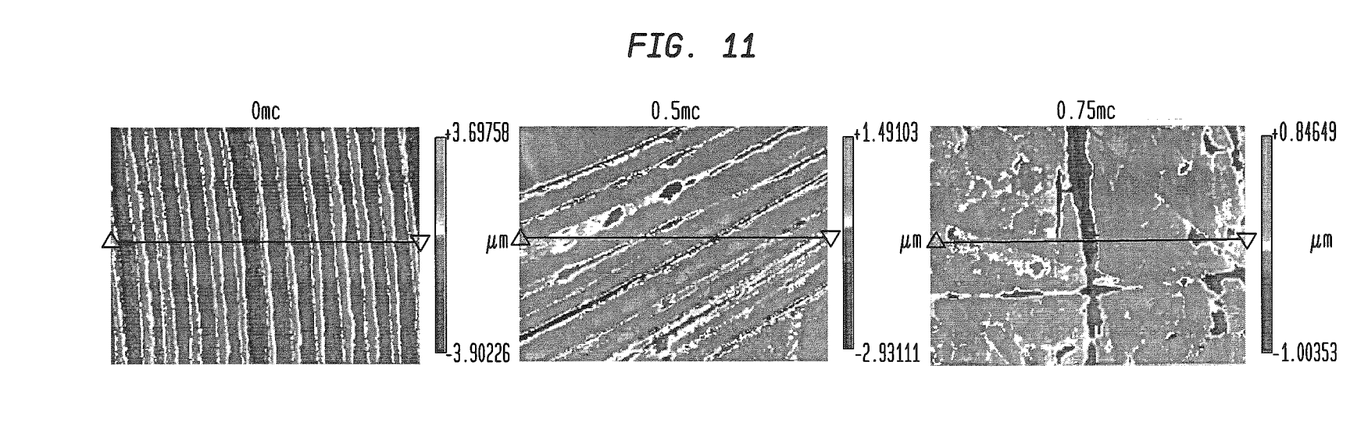

Machining marks as shown in FIG. 10 were still visible at 3.5 million cycles. As shown in FIG. 11 marks are no longer visible at 0.75 million cycle with CoCr heads due to the higher wear rate.

Figure 12:
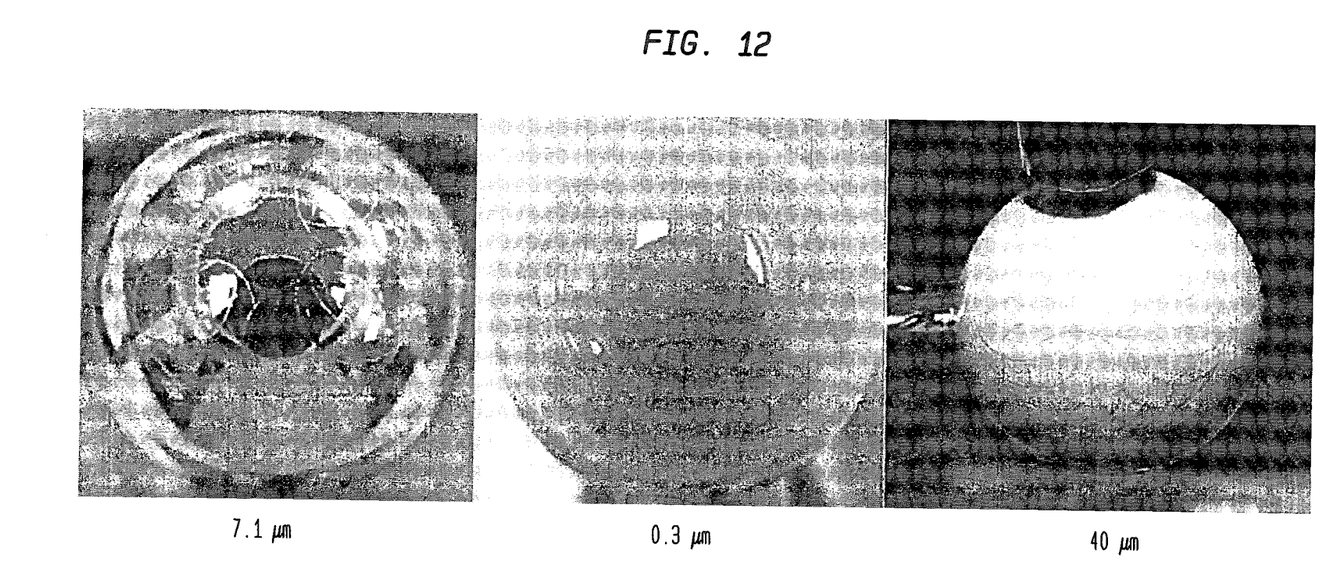
FIG. 12 are photographs of the CoCr, Delta and PEEK heads after testing.
Figure 13:
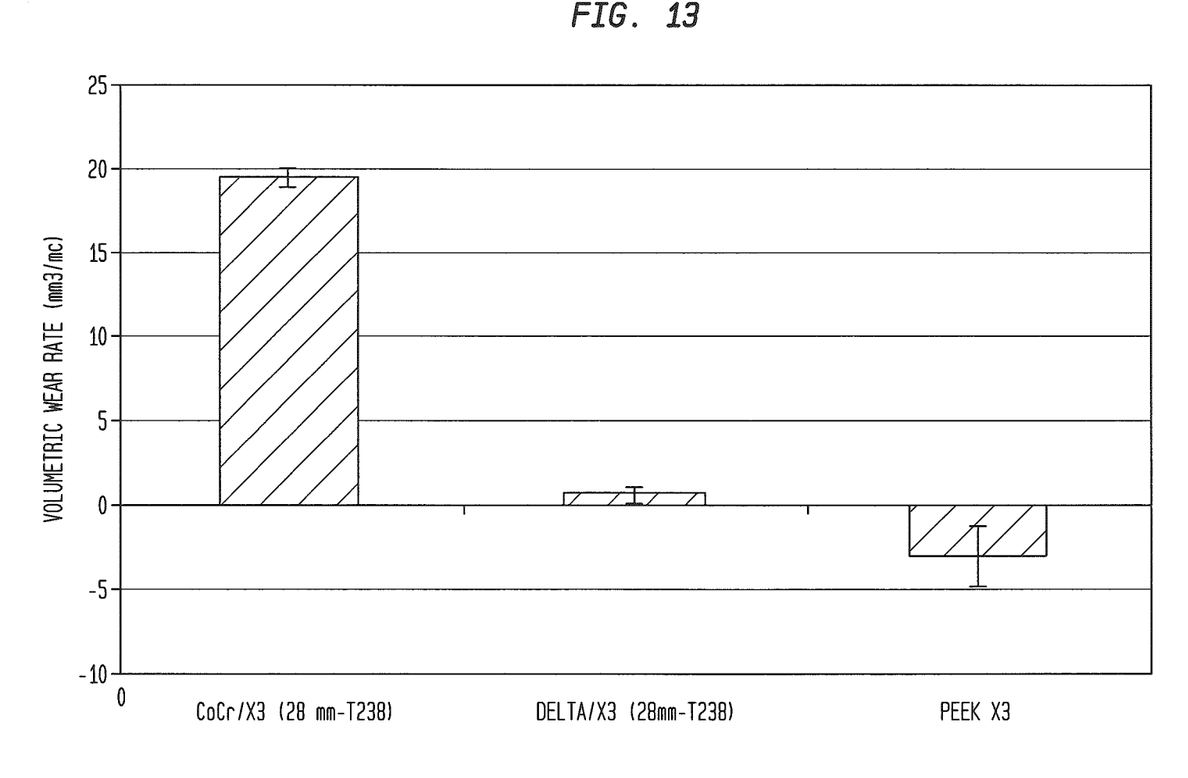
FIG. 13 shows wear rates of scratched (using diamond indentor) CoCr, Delta and PEEK heads against X3™ UHMWPE cups.

In this same study, three PEEK heads were scratched utilizing the previously established diamond indenter method (30N, 'spiral' pattern). These heads showed significant damage of approximately 40 μm PV (compared to 7.1 μm for CoCr and 0.3 μm for Delta) as shown in FIG. 12. These heads were then utilized for wear testing for 4.5 million cycles against X3™ cups. Wear rates were −3.1 mm³/MC after 4.5 million cycles (SD 1.827; n=3) for PEEK/X3 couples. At the same cycle count, this is not statistically different from the unscratched PEEK/X3™ bearing (p=0.353). In comparison, scratched 28 mm CoCr components exhibited 19.6 mm³/mc wear rate (SD 0.5; n=2) and scratched 28 mm Delta components exhibited 0.58 mm3/mc wear rate (SD 0.43; n=2 in a previously published study as shown in FIG. 13.

CoCr and Delta data were taken from a previous study published as Lee, R. et al., "Scratch and wear performance of prosthetic femoral head components against crosslinked UHMWPE sockets, Wear 267, pages 1915-1921, 2009.

Additionally, three 40 mm PEEK heads were tested against 44 mm F size X3 inserts. This study was used to determine wear rates in a higher stress non conforming bearing situation. At 1.0 million cycles, wear rates for this bearing were 0.60 mm3/mc (SD 503).

PEEK head wear has not yet been quantitatively measured. Utilizing a PEEK head on N2\Vac cups shows a significant 45% reduction in wear. Wear rates were negative for PEEK heads on X3™ cups. Wear rates were unchanged when the PEEK head was severely abraded. Wear rates remained near zero (but positive) when testing a non-conforming (40 mm PEEK head on 44 mm X3™ cup) geometry. PEEK head wear will be assessed after testing is completed.

Pure PEEK on UHMWPE all polymer bearing system (soft on soft) has shown unexpected results such as lower wear rates than CoCr on UHMWPE, regardless whether the PEEK femoral head is scratched or not.

Other companies which supply PAEK are BASF, Ultra-PAEK, PEKEKK; Dupont, Ureton PEKK, Declar; OPM, Oxford Performance Materials, Inc. PEKK; Hoechst Celanese (Hostatec)—PEEKK 5 and ICI (Vitrex), PEK and PEEK. Medical grade PEEK suppliers are ICI, Invibo, Solvay and Evonik.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic prosthetic hip or knee joint comprising:
a first prosthetic bearing component capable of being mounted on a femur of a hip or knee joint, the first bearing component having a bearing surface made of a substantially pure non-fiber reinforced polymer selected from the group consisting of polyetheretherketone (PEEK), polyether ketone (PEK), polyetherketoneketone (PEKK) and polyarylether-ketone-ether-ketone-ketone (PEKEKK); and
a second prosthetic bearing component capable of being mounted on an acetabulum or proximal tibia, the second prosthetic bearing having a bearing surface in sliding contact with the bearing surface of the first prosthetic bearing component, the bearing surface of the second bearing component made of ultra-high molecular weight polyethylene (UHMWPE) cross-linked by irradiation, the first prosthetic bearing component having a higher Shore D hardness than the second prosthetic bearing component.

2. The orthopedic prosthetic joint as set forth in claim 1, wherein the UHMWPE is cross-linked at least three times by irradiation, heating after irradiation and cooling after each heating.

3. The orthopedic prosthetic joint as set forth in claim 1 wherein the first bearing component consists essentially of a layer of the polymer coated, molded or grafted onto a substrate.

4. An orthopedic prosthetic joint comprising:
a first prosthetic bearing component capable of being mounted on a femur bone of a human hip or knee, the first bearing joint having a bearing surface consisting essentially of a substantially pure non-fiber reinforced PEEK; and a second prosthetic bearing component capable of being mounted on an acetabulum or proximal tibia, of the hip or knee joint, the second bearing having a bearing surface in sliding contact with the bearing surface of the first bearing component, the bearing surface of the second bearing component made of ultra high molecular weight polyethylene (UHMWPE) crosslinked by irradiation, the PEEK having a Shore D hardness higher than the UHMWPE.

5. The orthopedic prosthetic joint as set forth in claim 4, wherein the UHMWPE is cross-linked at least three times by irradiation, heating after irradiation and cooling after each heating.

6. The orthopedic prosthetic joint as set forth in claim 4 wherein the first bearing component consists essentially of a layer of the non-fiber reinforced PEEK coated, molded or grafted onto a substrate.

7. The orthopedic prosthetic joint as set forth in claim 4 wherein the PEEK has a hardness of about shore D 85 and the UHMWPE has a hardness of about shore D 70.

8. An orthopedic prosthetic hip or knee joint comprising:
a first prosthetic bearing component capable of being mounted on a femur, the bearing component having a bearing surface composed of substantially pure non-fiber reinforced PEEK polymer; and
a second prosthetic bearing component capable of being mounted on an acetabulum or a proximal tibia having a bearing surface in sliding contact with the bearing surface of the first prosthetic bearing component, the bearing surface of the second bearing component made of ultra-high molecular weight polyethylene (UHMWPE) crosslinked by irradiation, the PEEK polymer having a higher Shore D hardness than the UHMWPE.

9. The orthopedic prosthetic joint as set forth in claim 8, wherein the UHMWPE is cross-linked at least three times by irradiation, heating after irradiation and cooling after each heating.

10. The orthopedic prosthetic joint as set forth in claim 8 wherein the first bearing component consists essentially of a layer of PEEK coated, molded or grafted onto a solid or porous polymer composite substrate.

11. The orthopedic prosthetic joint as set forth in claim 8 wherein the first bearing component consists essentially of a layer of PEEK coated, molded or grafted onto a solid or porous metallic substrate.

12. The orthopedic prosthetic joint as set forth in claim 8 wherein the first bearing component consists essentially of a layer of PEEK coated, molded or grafted onto a solid or porous ceramic or ceramic composite substrate.

13. The orthopedic prosthetic joint as set forth in claim 8 wherein the PEEK has a hardness of about shore D 85 and the UHMWPE has a hardness of about shore D 70.

* * * * *